United States Patent [19]

De Vincentiis

[11] Patent Number: 4,503,076
[45] Date of Patent: Mar. 5, 1985

[54] VASODILATOR COMPOUND AND PHARMACEUTICAL COMPOSITIONS THEREFROM

[75] Inventor: Leonardo De Vincentiis, Rome, Italy

[73] Assignee: Ausonia Farmaceutic s.r.l., Rome, Italy

[21] Appl. No.: 424,516

[22] Filed: Sep. 27, 1982

[30] Foreign Application Priority Data

Dec. 1, 1981 [IT] Italy .............................. 25374 A/81

[51] Int. Cl.$^3$ ................... A61K 31/155; C07C 123/00
[52] U.S. Cl. ............................. 514/631; 260/501.14; 564/245
[58] Field of Search ............... 564/244, 245; 424/326; 260/501.14

[56] References Cited

U.S. PATENT DOCUMENTS 3,206,468  9/1965  Grenda ................................ 564/244
4,277,487  7/1981  Stahle et al. ........................ 564/244

OTHER PUBLICATIONS

Fernandes, Michael et al., *J. Lab. Clin. Med.*, vol. 87, (1976), pp. 561–567.

Fastier, F. N. et al., *J. Pharmacol. Exp. Ther.*, vol. 89, (1947), pp. 256–270.
Jen, Timothy et al., *Chemical Abstracts*, vol. 82, (1975), #106189b, Cumm. Index 1972–1976 at p. 15285CS.

*Primary Examiner*—Natalie Trousof
*Assistant Examiner*—L. Hendriksen
*Attorney, Agent, or Firm*—Bucknam and Archer

[57] ABSTRACT

The compound N-(2,6-dichlorophenyl)acetamidine

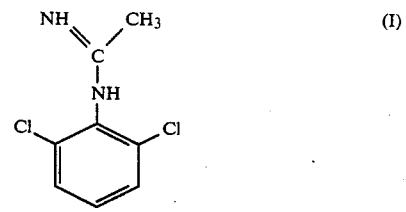

and its addition salts with pharmaceutically compatible inorganic and organic acids, exhibit a fast, strong vasodilator and antihypertensive action, which is of prolonged duration.

7 Claims, No Drawings

VASODILATOR COMPOUND AND PHARMACEUTICAL COMPOSITIONS THEREFROM

The present invention relates to hypertension and more specifically to compounds having vasodilator and anti-hypertensive activity.

It is well-known in the field of hypertension that the active compound should be not only fast-acting, but also that the activity should be prolonged.

An object of the present invention is to provide a compound which exhibits fast and prompt action and a compound the activity of which at the same time is subtantially prolonged so that it is not necessary to repeat the administration very frequently.

Another object of the present invention is to provide pharmaceutical compositions containing the active ingredient. Still another object of the present invention is to provide a process of preparation of the novel compound of this application.

The compound in accordance with the present invention is N-(2,6-dichlorophenyl)acetamidine of formula (I):

In addition to the compound of formula (I), addition salts of this compound with inorganic acids and pharmaceutically acceptable organic acids also fall within the scope of the present invention. Among the acids there may be mentioned for instance, hydrochloric acid, sulfuric acid, phosphoric acid, nitric acid, etc. The acid addition salts may also be formed with organic acids such as acetic acid, maleic acid, fumaric acid, malic acid, citric acid, etc.

The pharmaceutical compositions according to the present invention contain as the active ingredient the novel compound of formula (I) or one of its pharmaceutically acceptable salts, together with inert excipients.

In accordance with the present invention, the compound of formula (I), which will be represented hereinbelow by the symbol AF 544, is prepared by reaction of acetonitrile (II) with 2,6-dichloroaniline (III) in the presence of a catalyst, which is preferably a Lewis acid. Particularly suitable is aluminum trichloride. The reaction scheme is represented hereinbelow:

The reaction is preferably carried out in the absence of a solvent, in the temperature range of 50°–180° C. and still more advantageously in the range of 100°–150° C. The following example illustrates the process according to the present invention, but is not intended to limit the scope.

EXAMPLE

Acetonitrile in the amount of 14.9 grams (0.36 moles) is added to 58.32 grams, (0.36 moles) of 2,6-dichloroaniline. To the reaction mixture is added under mechanical stirring during the course of thirty minutes, aluminum trichloride in the form of a powder in the amount of 48 grams, (0.36 moles). The reaction mixture is allowed to react for two hours at 140° C. At the end of this period, the hot mixture is poured into a solution of 400 cc of water and 20 cc of concentrated hydrochloric acid while making sure that the pH of the mixture remains acidic. Decolorizing carbon in the amount of 10 grams is then added, the mixture is allowed to cool and finally is filtered by suction. To the filtrate is added 140 cc of 30% NaOH until the pH is basic.

The reaction mixture is extracted with chloroform, dried over anhydrous sodium sulfate and the solvent is allowed to evaporate under vacuo. The product is recrystallized from hot diisopropyl ether, melting point 111°–113° C. Yield of crystalline product: 48%.

From the product of formula (I) thus obtained, the corresponding salts may be prepared in a conventional manner. For instance, compound I may be dissolved in ether and the ether solution is then added to a solution of hydrogen chloride in ethanol, until the reaction is acidic. The hydrochloric salt precipitates in the form of colorless crystals of melting point 265°–267° C. The hydrochloride of the compound of formula (I) is soluble in water while the base on the other hand, is soluble by heating in common organic solvents.

The hydrochloride of the compound of formula (I) exhibits the following physical and chemical properties:

Elementary Analysis: Calcd. for $C_8H_9Cl_3N_2$ (Mol. Wt.=239.51). Found % C=40.11; H=3.78; N=11.69. Found % C=40.03; H=3.83; N=11.61.

I.R. Spectrum (nujol mull): 3230–2660 cm$^{-1}$ (enlarged band, N—H); 1670 cm$^{-1}$ (C=N); 1600 cm$^{-1}$ (C=C); 745 cm$^{-1}$ (C—H).

H$^1$NMR Spectrum (determined in hexadeuterodimethylsulfoxide, internal reference TMS): 1.4 δ(s, 3H, C—CH$_3$); 8.15–9 (m, 3H aromatic); 8.8–9.2 (m, 3H mobile).

By means of analogous reactions, it is possible to obtain also the following salts:
 maleate, m.p. 161°–164° C. (dec.);
 acid phosphate, $C_8H_{11}Cl_2N_2PO_4$, decomposition point 188°–191° C.;
 citrate, m.p. 158°–162° C.;

The experimental, analytical data for the salts are in agreement with the calculated values. The compound of formula (I), AF 544, has been used in pharmacological tests in the form of the hydrochloric salt.

Acute Toxicity

The DL$_{50}$ has been determined in mice by the oral as well as intraperitoneal route. The results are as follows:
 DL$_{50}$ (mice): orally 420 mg/kg; i.p.: 170 mg/kg.

Vasodilator Activity (Foster et al., J.Pharmacol.Exp.Ther. 89,256,1947)

This study has been carried out in rats by perfusion of the lower limb while determining the variation of the resistance offered by the vascular zone after the perfusion by means of a suitable pressure transducer.

The vaso-constricting agent used is a solution containing a high content of potassium, together with papaverine, the latter being used for comparison purposes. The results obtained are tabulated in Table I. The results show that AF 544 exhibits a substantial vasodilator activity, which is only slightly inferior to that of papaverine at equal dose.

Hypotensive Activity

The product has been administered by the intraperitoneal route to rats having normal blood pressure in the dose of 10 and 25 mg/kg. The systolic pressure of the animals has been measured 1, 4, and 24 hours respectively after the treatment using hydralazine in the dose of 1 mg/kg intraperitoneally for comparison. The results obtained are reported in Table II. The hypotensive activity of AF 544 depends on the dose and progressively increases after the first hour and reaches the maximum effect during the fourth hour. When the substance is administered in the dose of 25 mg/kg, the decrease in the systolic pressure is 2.5 times the decrease caused by hydralazine administered in the dose of 1 mg/kg. The decrease in pressure resulting from the administration of hydralazine occurs much more rapidly and reaches the maximum even during the first hour, but immediately thereafter decreases.

The kinetics of the hypotensive action of AF 544 represents a favorable aspect of the product being examined with respect to the substance used for comparison.

Antihypertensive Activity

There are utilized for this test rats having genetically high blood pressure. The rats are treated for three days with AF 544 in the dose of 25 mg/kg orally. After each treatment and specifically after 1, 4, 8 and 24 hours respectively, the systolic pressure of the animals is measured. The results shown in Table III demonstrate that the administration of AF 544 orally to rats which genetically have high blood pressure in the dose of 25 mg/kg, causes a decrease in the pressure present during the first hour and further that the decrease reaches its maximum between the fourth and eighth hour, the value remaining about the same during the twenty-fourth hour.

In a second experiment, the substance AF 544 has been administered to rats which have been treated to cause an increase in blood pressure, specifically by tying the abdominal aorta. The administration has been carried out by the oral route in the dose of 20 and 40 mg/kg respectively. Measurements of diastolic pressure, systolic pressure and average pressure are made after 1, 15, and 30 minutes. After 30 minutes, for each group, determinations are made of the hematic renin and the hematic angiotensin. The dose of 20 mg/kg is found to reduce the diastolic pressure of 10–15% while the systolic pressure and the average pressure remain unchanged. On the other hand, the dose of 40 mg/kg is found to be effective on all three parameters, causing an average reduction of about 25%. Further, it has been found that the activity of renin increases in proportion to the dose of AF 544 being used. It has also been found that an increase in the quantity of angiotensin occurs, which is inversely proportional to the dose of AF 544.

The Effect on the Circulation and on Breathing

For this test, six cats of both sexes are used. The animals had been brought to a state of anaesthesia by means of urethane. The substance AF 544 is administered by the endovenous route in the dose of 0.1–1 mg/kg. The following parameters have been studied: average arterial pressure, amplitude and respiratory frequency, effect on pressure responses to various agonists, (acetylcholine, adrenaline, occlusion of the carotid artery, and vagal stimulation).

The results obtained are summarized in Table IV.

The substance AF 544 exhibits a transitory hypotension, which is correlated to the dose administered, (13.9% and 46.0% respectively per 0.1 mg/kg and 1 mg/kg intravenously.

The variations of the other parameters observed are small and statistically they are not significant.

Spasmolytic Activity

The tests are carried out in vitro utilizing the isolated small intestine of guinea pigs. As agonist, there is used barium chloride in the dose of $2.10^{-6}$ g/cc. The substance AF 544 and papaverine, which is a substance having well-known spasmolytic activity, are tested in the same concentration of $10^{-6}$ g/cc. In this test, AF 544 exhibits a high spasmolytic activity with an efficacy which is statistically analogous to that of papaverine in the same concentration, (see Table V).

TABLE I

| | Vasodilator Activity of AF 544 on the lower limb of Rats after Perfusion | | | |
|---|---|---|---|---|
| SUBSTANCE | DOSE g/cc | NO. of ANIMALS | DECREASE IN PRESSURE mm Hg ± e.s | % |
| AF 544 | $5.10^{-5}$ | 10 | 60 ± 3.2 | 27.5 |
| PAPAVERINE | $5.10^{-5}$ | 10 | 82 ± 13.6 | 39.3 |

TABLE II

| | Hypotensive Activity of AF 544 in Rats Having Normal Pressure | | | | |
|---|---|---|---|---|---|
| TREATMENT | DOSE mg/kg i.p. | No. of Animals | Percentage Variation of Systolic Pressure with Respect to the Basal Values after Different Periods of Treatment | | |
| | | | 1 hour | 4 hours | 24 hours |
| CONTROL | — | 10 | +21.8 ± 9.8 | +9.6 ± 9.8 | −2.5 ± 17.5 |
| HYDRALAZINE | 1 | 10 | +21.0 ± 4.9 | −18.0 ± 3.1 | −7.5 ± 7.8 |
| AF 544 | 10 | 10 | −1.5 ± 1.8 | −13.1 ± 6.8 | Not Determined |
| AF 544 | 25 | 10 | −6.6 ± 13.4 | −46.2 ± 3.4 | −2.2 ± 2.8 |

TABLE III

Antihypertensive Activity of AF 544 Administered for Three Consecutive Days to Rats Which Genetically Exhibit High Blood Pressure

| DOSE mg/kg orally | Day of Treatment | Percentage Variation of Pressure with Respect to The Basal Values of the First Day After Different Periods of Treatment | | | |
|---|---|---|---|---|---|
| | | 1 hour | 4 hours | 8 hours | 24 hours |
| 25 | 1° | −5 | −20 | −18 | −19 |
| | 2° | −26 | −20 | −27 | −28 |

TABLE III-continued

Antihypertensive Activity of AF 544 Administered for Three Consecutive Days to Rats Which Genetically Exhibit High Blood Pressure

| DOSE mg/kg orally | Day of Treatment | Percentage Variation of Pressure with Respect to The Basal Values of the First Day After Different Periods of Treatment | | | |
|---|---|---|---|---|---|
| | | 1 hour | 4 hours | 8 hours | 24 hours |
| | 3° | −22 | −11 | −15 | −12 |

TABLE IV

Effect of AF 544 on the Circulation and on the Respiration of Anaesthesized Cats

| DOSE mg/kg i.v. | No. of Animals | EFFECT ON ARTERIAL PRESSURE | | RESPIRATION | | EFFECT IN % ON PRESSURE RESPONSES TO | | | |
|---|---|---|---|---|---|---|---|---|---|
| | | mm Hg ± e.s | % | Amplitude % | Frequency % | Acetylcholine | Adrenaline | Carotid Occlusion | Vagal Stimulation |
| 1 | 3 | −36.7 ±14.8 | −46.0 | +16.1 | −8.5 | +4.5 | +4.0 | +2.5 | +20.4 |
| 0.1 | 3 | −12.5 ±12.5 | −13.9 | +50.9 | +31.4 | +5.0 | −25.6 | +3.5 | +11.5 |

TABLE V

Spasmolytic Activity on the Ileum of Guinea Pigs "in vitro" Using $Cl_2Ba$ ($2.10^{-6}$ g/cc) as the Agonist- Period of Incubation: 1 Minute

| TREATMENT | NO. OF ANIMALS | CONCENTRATION in g/cc | % INHIBITION |
|---|---|---|---|
| AF 544 | 6 | $10^{-6}$ | 49.8 ± 7.44 |
| Papaverine | 6 | $10^{-6}$ | 73.7 ± 8.09 |

The present invention also covers all the industrial aspects connected with the use of AF 544 and its salts as antihypertensive agents. It is, therefore, one aspect of the present invention to provide pharmaceutical formulations which contain predetermined amounts of AF 544 or its salts. The substances according to the present invention may be administered by the oral route, for instance in the form of compresses, capsules, drops, and syrups. The following formulations may be mentioned by way of example:

(a) compresses containing between 1 and 25 mg of AF 544 as the hydrochloride with excipients and dispersing agents commercially used in the pharmaceutical industry such as (b) opercolated gelatinous capsules containing between 1 and 25 mg of AF 544 as the hydrochloride;

(c) drops: a mixture of water, alcohol, and glycerol containing 0.2–2.5% of AF 544 as the hydrochloride is used;

(d) a syrup containing between 0.02 and 0.5% of AF 544 as the hydrochloride.

What is claimed is:

1. A compound selected from the group consisting of N-(2,6-dichlorophenyl)acetamidine of formula (I)

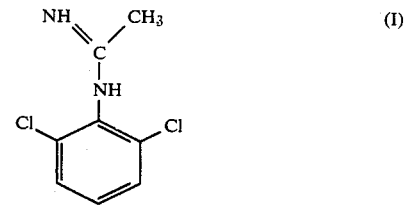

and its addition salts with pharmaceutically compatible inorganic or organic acids.

2. A compound according to claim 1 wherein the inorganic and organic acids are selected from the group consisting of hydrochloric acid, sulfuric acid, nitric acid, phosphoric acid, acetic acid, maleic acid, fumaric acid, malic acid, and citric acid.

3. A pharmaceutical composition having vasodilator activity, for lowering the blood pressure in a living subject which contains a therapeutically effective amount per unit dosage form of N-(2,6-dichlorophenyl)acetamidine of formula (I) or an addition salt thereof with a pharmaceutically acceptable organic or inorganic acid and inert ingredients.

4. The composition according to claim 3 which is in the form of compresses containing 1–25 mg of the hydrochloride of compound (I) per unit dosage form.

5. The composition according to claim 3 which is in the form of capsules containing between 1 and 25 mg of the hydrochloride of compound (I).

6. The composition according to claim 3 in the form of drops containing 0.2–2.5% of the hydrochloride of compound (I) in a solution containing a mixture of water, alcohol, and glycerine.

7. The composition according to claim 3 in the form of a syrup containing 0.02–0.5% of the hydrochloride of compound (I).

* * * * *